United States Patent [19]
Sellers

[11] 4,234,309
[45] Nov. 18, 1980

[54] DENTAL TWIST LOCK PIN AND WRENCH

[76] Inventor: Wm. Ralph Sellers, 35B Codd Blvd., Langley AFB, Va. 23665

[21] Appl. No.: 51,316

[22] Filed: Jun. 22, 1979

[51] Int. Cl.³ .............................................. A61C 5/04
[52] U.S. Cl. ................................... 433/225; 433/174; 433/127; 279/1 S
[58] Field of Search ..................... 433/225, 174, 127; 279/1 S

[56] References Cited

U.S. PATENT DOCUMENTS

| | | | |
|---|---|---|---|
| 517,248 | 3/1894 | Stanbrough | 433/127 |
| 2,351,232 | 6/1944 | Schnabolk | 279/1 S |
| 3,395,455 | 8/1968 | Overby et al. | 433/225 |
| 3,813,779 | 6/1974 | Tosti | 433/224 |
| 4,103,422 | 8/1978 | Weiss et al. | 433/174 |

FOREIGN PATENT DOCUMENTS 2395738  3/1979  France .................................... 433/174

OTHER PUBLICATIONS

"Leakage around various types of retention pins", J. of Prosthetic Dent., Feb., 1975, p. 192, Chan et al.

Primary Examiner—Louis G. Mancene
Assistant Examiner—John J. Wilson
Attorney, Agent, or Firm—Joseph E. Rusz; Arsen Tashjian

[57] ABSTRACT

A twist-lock pin for improving the retention and resistance characteristics of plastic dental restorative materials and a wrench for providing positive control over the pin during insertion into the opening in the tooth. The pin is partially screwed counter-clockwise into a left-hand threaded metal cylinder, the wrench body. After two revolutions, the pin bottoms out against a flat ended, right-hand limiting screw which is inserted clockwise from the opposite end of the wrench body and which is limited by two lands, one a flat area in the wall of the wrench body and the other at the end of the wrench body. After the wrench has been utilized to insert the pin into the tooth structure, it is removed by relieving the pressure on the pin and unscrewing the wrench from the pin.

2 Claims, 2 Drawing Figures

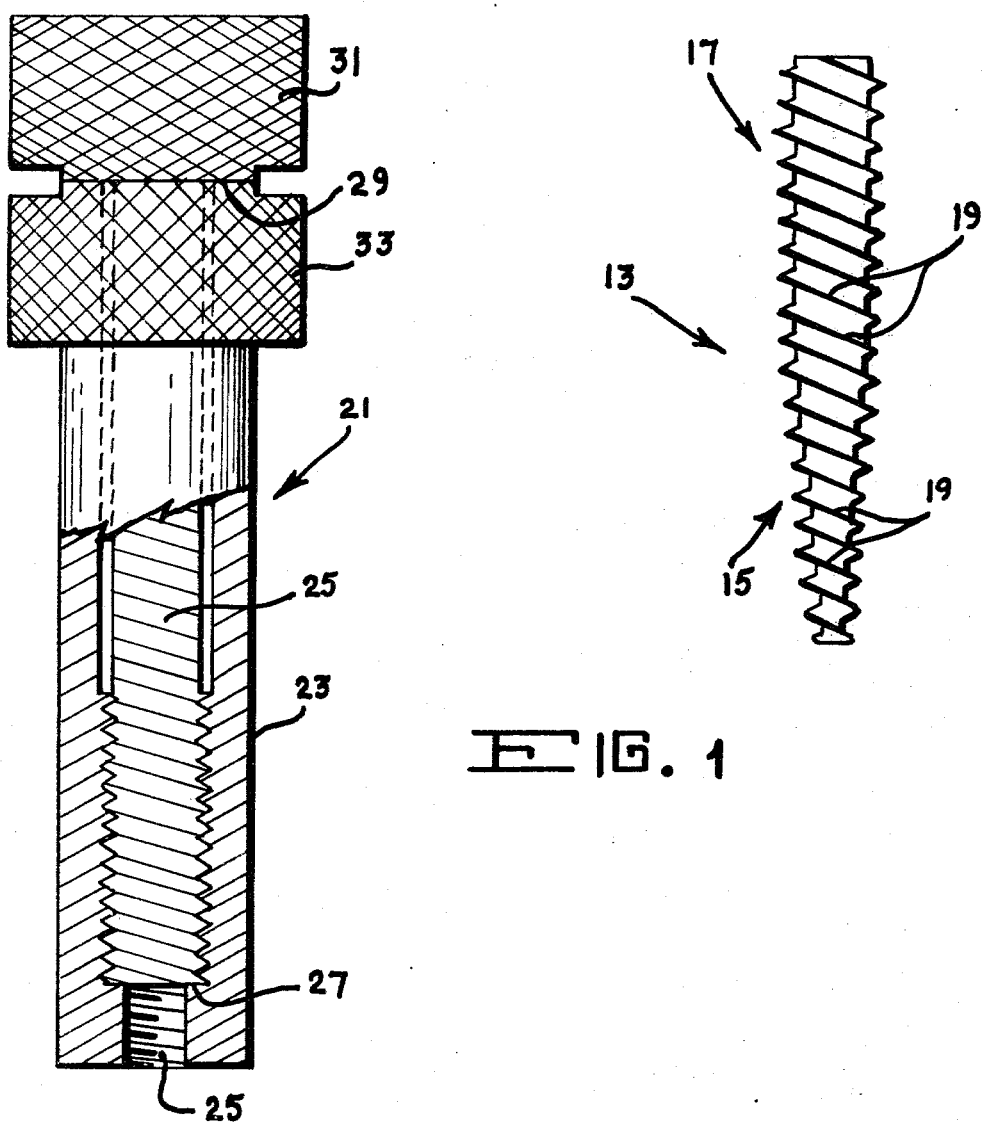

DENTAL TWIST LOCK PIN AND WRENCH

STATEMENT OF GOVERNMENT INTEREST

The invention described herein may be manufactured and used by or for the Government for governmental purposes without the payment of any royalty thereon.

REFERENCE TO RELATED PATENT APPLICATION

Reference is made to my copending patent application Ser. No. 51,317, filed on even date herewith which describes and claims a drill for use in preparing the tooth for receiving the twist-lock pin using the wrench hereinafter described.

BACKGROUND OF THE INVENTION

This invention relates to a twist-lock pin and wrench for inserting the pin into a tooth and, more particularly, the invention is concerned with providing a tapered left-hand threaded pin for insertion into a drilled hole in a tooth with a wrench which permits positive control of the pin during insertion.

Heretofore, it has been common practice to anchor a superstructure to the understructure of a tooth by drilling one or more holes into the tooth or understructure. A pin or rod is inserted in each of the holes and allowed to extend above the understructure so that the exposed portion of the pin may be used to anchor the superstructure onto the tooth. The pins are relatively small in diameter and difficult to handle. It is especially difficult to insert the pin in the hole where the hole is undersized and the pin is threaded. An example of a prior art device is described in U.S. Pat. No. 3,434,209 and is manufactured and distributed by Whaledent International of New York, N.Y. In this prior art device called the T.M.S. system, the pin requires ten complete revolutions to seat a distance of 1 mm. Also, the tool for inserting the T.M.S. pin is a slotted screwdriver design which does not hold the pin securely causing problems during initial pin insertion. This can lead to unwanted pin shear and uneven stress loading of the tooth structure if the pin is not in exact alignment in the hole.

What is needed is a dental anchor pin which can be easily inserted into the opening in the tooth with a minimum of rotation being required. The pin should be easier to align in the tooth opening with positive control of the pin during insertion. Also, the rate of loading of the pin should be more rapid than presently available pins in order to provide the operator with greater "feel" and ability to forecast and prevent ultimate torsion failure.

The hereinafter described twist-lock pin and wrench disclose a system which will provide all of the desired features noted above. The pin is easier to insert since the tip of the pin is smaller than the surface diameter of the pin hole in the tooth. The pin seats in a counter-clockwise rotation and less than one 360° rotation is required to fully seat the pin in the tooth opening. Also, because of the counter-clockwise rotation of the pin, the action of the cut-off bur which rotates clockwise, serves to seat the pin deeper and more securely in the tooth rather than loosen it when the excess portion of the pin is reduced.

SUMMARY OF THE INVENTION

The present invention is concerned with providing a twist-lock pin and wrench for improving the retention and resistance characteristics of plastic dental restorative materials. A tapered hole is drilled into sound tooth structure whereupon a geometrically similar, but oversized, threaded pin is inserted. Slight rotation of the pin in a counter-clockwise manner causes the threads to bite simultaneously, effectively locking it into place. The wrench which is used to insert the pin into the tooth provides positive control of the pin during insertion, yet the wrench is easily removed from the pin.

Accordingly, it is an object of the invention to provide a dental twist-lock pin and wrench wherein the pin is taper fitted into a geometrically similar but undersized hole allowing all threads to bite simultaneously and requiring less than 360° rotation to fully seat.

Another object of the invention is to provide a dental twist-lock pin and wrench system wherein the pin includes a left-hand thread and seats with counter-clockwise rotation so that the action of a clockwise rotating bur which may be used to reduce excess, only tends to seat the pin deeper rather than unscrew it.

Still another object of the invention is to provide a dental twist-lock pin and wrench arrangement wherein all threads bite simultaneously so that the stresses are evenly distributed to surrounding tooth structure.

A further object of the invention is to provide a dental twist-lock pin threaded for insertion into a tooth drilled with a geometrically similar drill to form a tapered hole. The pin self-aligns in the tapered hole and employs double lead screws to increase thread area.

A still further object of the invention is to provide a dental twist-lock tapered pin and wrench wherein the time necessary for insertion into the tooth is reduced because less screwing is required and the tip of the pin is small relative to the surface diameter of the pin hole.

Another still further object of the invention is to provide a dental twist-lock pin and wrench system whereby the rate of loading as perceived by the operator is more rapid than conventional non-tapered pins, providing the operator with greater "feel" and ability to forecast ultimate torsion failure.

These and aother objects, features and advantages will become more apparent after considering the following detailed description taken in conjunction with the annexed drawings and appended claims.

BRIEF DESCRIPTION OF THE DRAWING

FIG. 1 is a side view of a tapered twist-lock pin having a left-hand thread according to the invention for insertion into a tapered opening in a tooth; and FIG. 2 is a view in side elevation in partial section of a wrench according to the invention for holding the pin of FIG. 1 during insertion into the drilled tooth.

DESCRIPTION OF A PREFERRED EMBODIMENT

Referring now to the drawings, there is shown in FIG. 1 a threaded pin 13 including a lower tapered portion 15 and a straight untapered upper portion 17. The tapered portion 15 of the pin 18 is slightly oversized so as to be a tight fit in a hole in the tooth made by a drill of similar geometric configuration. The pin 13 includes a number of threads 19 along the length thereof for gripping the sides of the tapered hole in the tooth and effectively locking it into place. The threads 19 are preferably left-hand so that rotation in a counter-clockwise direction will cause the pin 13 to seat firmly in the drilled hole. Since the lower portion 15 of the pin 13 is tapered, only a slight rotation in the counter-clockwise direction will lock it into place. Plastic restorative materials such as dental amalgam, composites, silicates, resins and gold foil, may be inserted against the straight threaded protruding portion of the pin 13, thus enhancing its retention and resistance characteristics.

The twist-lock tapered pin 13 differs from existing pin designs in that both the pin and the pin-hole are tapered. This allows the pin 13 to freely enter the pin-hole for approximately 75% of its depth before rotation is begun. The design of the thread 19 includes an extremely steep pitch to provide rapid seating of the pin 13. In order to increase the thread area available for retention, two sets of threads are used which are parallel and independent forming double lead screw threads. All other threaded pins employ a single continuous thread of lesser pitch.

A wrench 21 which allows precise control over the pin 13 during insertion is shown in FIG. 2. The pin 13 is partially screwed counter-clockwise into a left-hand threaded metal cylinder, the wrench body 23 in the threaded opening 25. After two revolutions, the pin 13 bottoms out against a flat ended, right hand limiting screw 25 which is inserted clockwise from the opposite end of the wrench body 23 and which is limited by a first land 27, in the form of a shoulder in the wall of the wrench body 23 and a second land 29 at the upper end of the wrench body 23.

In operation, the right-handed limiting screw 25 is rotated until it contacts the lands 27 and 29. The pin 13 is then threaded into the opening 25 in the lower end of the wrench body 23 until it contacts the lower end of the limiting screw 25. The wrench 21 is utilized to insert the pin 13 into the tooth structure. The limiting screw 25 is backed off counter-clockwise to remove pressure from the head of the pin 13. It should be noted that retraction of the limiting screw 25 is effected by counter-clockwise rotation of its knurled knob 31 while holding the knurled knob 33 on the wrench body 23 from turning. This rotation of the limiting screw 25 tends to further seat the pin 13 in the tooth rather than unscrew it and since backing off the limiting screw 25 removes all pressure from the head of the pin 13, the wrench 21 can be easily removed from the pin 13.

Although the invention has been illustrated in the foregoing specification in terms of a preferred embodiment thereof, the invention is not limited to this embodiment or to the particular configuration shown and described. It will be apparent to those skilled in the art that certain changes, modifications and substitutions can be made with respect to the shape of the elements without departing from the true spirit and scope of the appended claims. It can be seen that the invention may be used in the same manner that conventional bonded, threaded, and cemented pins are used to enhance the retention characteristics of plastic dental restorative materials and tooth structure.

Having thus set forth the nature of my invention, what I claim as now and desire to secure by Letters Patent of the United States is:

1. In combination, a twist-lock pin for insertion into a tapered hole drilled into sound tooth structure and a wrench for holding the pin during insertion, said twist-lock pin having a left-hand thread on the outer surface thereof, said twist-lock pin having a tapered lower portion for engagement with the drilled tooth and a straight threaded upper portion for threadable engagement with the wrench; and said wrench comprising a wrench body of substantially cylindrical configuration with a left-hand threaded opening in the lowermost end thereof, the upper portion of said twist-lock pin being in threadable engagement with the left-hand threaded opening in said wrench body, the lower portion of the inner surface of said wrench body having right-hand threads thereon, a limiting screw having right-hand threads on the outer surface of the lower portion thereof for engagement with the right-hand threads in the lower portion of said wrench body, means for limiting the travel of said limiting screw in said wrench body so that the lowermost surface of said limiting screw is in direct contact with the uppermost surface of said twist-lock pin thereby allowing positive control over said twist-lock pin during insertion into the drilled hole in the tooth and easy separation of the wrench from the pin without loosening the pin from its position in the tooth.

2. The combination defined in claim 1 wherein said means for limiting the travel of said limiting screw in said wrench body includes a first land in the form of a shoulder in the wall of said wrench body near the lower end thereof and a second land on the upper end surface of said wrench body, the lower end surface of said limiting screw contacting said first land and preventing further downward movement of said limiting screw.

* * * * *